United States Patent [19]

Ishimura et al.

[11] Patent Number: 5,471,986
[45] Date of Patent: Dec. 5, 1995

[54] METHOD OF ANGIOGRAPHY

[75] Inventors: Takao Ishimura, 302, 16-17, Sumiyoshi Honcho 3-chome, Nada-ku, Kobe-shi, Hyogo-ken; Hiroyuki Mitsuhashi, Yokohama, both of Japan

[73] Assignees: Takao Ishimura; Fuji Systems Kabushiki Kaisha, both of Japan

[21] Appl. No.: 265,643

[22] Filed: Jun. 24, 1994

[30] Foreign Application Priority Data

Jun. 30, 1993 [JP] Japan ................................. 5-161700

[51] Int. Cl.⁶ .................................................. A61B 6/00
[52] U.S. Cl. ........................................ 128/658; 128/656
[58] Field of Search ................................. 128/656–658; 604/49–56, 280, 282

[56] References Cited

U.S. PATENT DOCUMENTS

| | | | |
|---|---|---|---|
| 4,909,258 | 3/1990 | Kuntz et al. | 128/658 |
| 4,961,731 | 10/1990 | Bodicky et al. | 604/264 |
| 4,983,169 | 1/1991 | Furukawa | 604/164 |
| 5,188,619 | 2/1993 | Myers | 604/280 |
| 5,203,776 | 4/1993 | Durfeee | 604/264 |

*Primary Examiner*—John D. Yasko
*Assistant Examiner*—Adam J. Cermak
*Attorney, Agent, or Firm*—Gifford, Krass, Groh, Sprinkle, Patmore, Anderson & Citkowski

[57] ABSTRACT

A method of angiography which reduces the patient's burden due to the surgery. By replacing catheters and by means of brachial paracentesis, angiography is performed on each of coronary artery, vein bypass, gastroepiploic artery and internal thoracic artery, through the steps of: puncturing a paracentetic tube into the brachial artery, and inserting through the tube a catheter selected from the following group: (a) a catheter of the type in use for the left and right coronary artery and the venous bypass; (b) a catheter of the type in use for the internal thoracic artery; and (c) a catheter of the type in use for the gastroepiploic artery.

2 Claims, 1 Drawing Sheet

METHOD OF ANGIOGRAPHY

BACKGROUND OF THE INVENTION

1. Field of the Invention

The present invention relates to a method of angiography of coronary arteries, vein bypasses, gastroepiploic arteries and internal thoracic arteries.

2. Description of the Prior Art

In accordance with the increasing cases of percutaneous angiography or coronary arterial bypass surgeries, cases of repeating coronary arterial and bypass angiography have increased. Also, in the western countries, for the purpose of cost saving of medical expenses, increasing numbers of coronary artery angiography cases have been performed in outpatient sites.

Conventionally, coronary artery angiography has employed two methods. The first method, termed the "Judkins" method, comprises the step of puncturing a paracentetic tube into the femoral artery, from which a catheter is inserted. The second method, termed the "Sones" method, comprises the step of incising the skin of the brachial region to expose the artery, to which a hole is formed to be inserted by a catheter.

Advantages and disadvantages of the prior art are as follows. In the Judkins method, performed only by puncture of a paracentetic tube into a blood vessel, compared to the Sones method performed by incision of the vessel, damage to skin and vessels is minimized. Also, insertion of a catheter from the paracentetic tube into the blood vessel minimizes damage to the blood vessel caused by entrance and exit of the catheter.

Since the process is perfomed without incision of cortex and blood vessel, no wound or adhesion of wound region remains. Therefore, even in angiography which requires frequent repetition of angiographic processes, it is advantageous to repeat such processes from the same region.

In the Judkins method, the catheter used is preformed to easily enter the coronary artery, and may be operated by a beginner with only relatively short-term training.

On the other hand, one disadvantage of the Judkins method is that the patient would feel ashamed because the catheter is inserted from the femoral region.

Since the paracentetic tube is punctured, its removal often causes bleeding, necessitating a long recovery period.

For angiography of the left and right coronary arteries and venous bypass, separate catheters are employed, respectively. Necessary replacement of the catheters is time consuming and increases the costs associated with performing angiography. Moreover, the Judkins method cannot be employed for cases of arterial obliteration, such as stenosis in the gastroepiploic artery or femoral artery.

Concerned with cost saving, most western countries are hesitant to perform the Judkins method even though there are increasing cases for performing coronary artery angiography in outpatient sites or mobile angiography in automobiles.

In the Sones method, the brachial region is incised to expose the artery, and a catheter is inserted in the opening. By using a brachium, the patient does not feel ashamed.

After an angiograph is performed, the opening is seamed. Since the incised region is in the brachium, recovery time required after angiography is reduced to one hour or less. Moveover, only one catheter is used for forming angiograph of both the right coronary artery and the venous bypass.

A disadvantage of the Sones method is that the patient necessarily must undergo surgery and suffers from the burden and the time necessary for the operation. Also, the incised cortex causes the vessel to be exposed leaving a wound and adhesion. As a result, the incision cannot be done at the same region, and repeated angiographic operations must be done in shifted positions, thereby the region to be incised is limited in repeated cases. In addition, the techniques of cutaneous incision or insertion of the catheter into the coronary artery or bypass are so difficult that they require a one to two year period of time to acquire the technique. Cost concerns in most western countries also cause performing the Sones method to be prohibitively expensive although there are increased cases for performing coronary artery angiography in outpatient sites.

SUMMARY OF THE INVENTION

The present invention is to provide a method of angiography of a coronary artery, a venous bypass, a gastroepiploic artery, or an internal thoracic artery by means of brachial paracentesis comprising the steps of puncture from the paracentetic tube by an improved thin catheter as follows:

(a) a catheter of the type "a" in use for the left and right coronary artery and the venous bypass;

(b) a catheter of the type "b" in use for the internal thoracic artery; and (c) a catheter of the type "c" in use for the gastroepiploic artery.

The catheters above are, as shown in FIG. 1, those manufactured, for example, by the Applicants, as Interbeck type heart-use catheters.

DETAILED DESCRIPTION OF THE INVENTION

Figure 1:
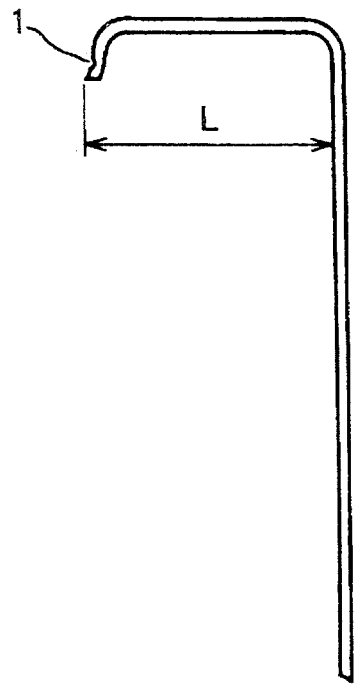
FIG. 1 is a front view of a catheter of type "a"
Figure 2:
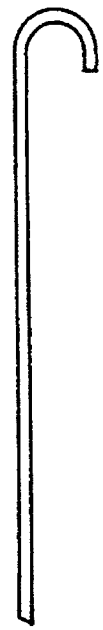
FIG. 2 is a front view of a catheter of type "b"
Figure 3:
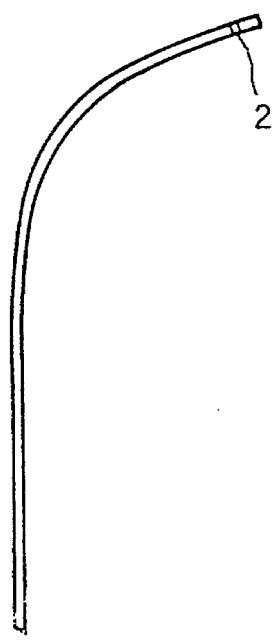
FIG. 3 is a front view of a catheter of type "c".

Type "a" catheter, is thinned as 2 Fr and 5. 2 Fr, 800 mm in length, and 35 mm and 40 mm in the end length L, to facilitate a rotational operation. The tip end thereof is a soft tip, and formed with an opening. In addition, one or two side holes 0.1 to 1.5 mm in diameter are formed 2 to 10 mm from the tip (not shown) to provide increased safety, and also provide a circular section to facilitate flow of the angiographic agent.

Type "b" catheter is designed to be inserted from the brachium, which is properly used for performing an internal thoracic arterial angiography, formed with its length of 800 mm, and can be easily and most selectively inserted within the internal thoracic artery.

Type "c" catheter is designed to be also inserted from the brachium, which is properly used for performing a gastroepiploic arterial angiograpy, and 800 mm in length. Its one end is open, on the side of which a hole 2 of 0.1 to 1.5 mm in diameter is formed at 2 to 20 mm apart from the tip end. It is shaped similarly to the Sones catheter, but is formed to have the length and shape of its tip end conformed to easily engage with the exit of the femoral artery. In addition, by using a guide wire, this catheter can be properly and most selectively inserted within the gastroepiploic artery.

The comparison between the angiography according to the invention and those of Judkins' and Sones' methods is shown in Table 1.

TABLE 1

Comparison between Methods of Angiography

| Sones' Method | Judkins' Method | Invention's Method |
|---|---|---|
| Approached from brachial artery. | Approached from right/left femoral artery. | Approached from right/left brachial artery. |
| Percutaneous incision. Using Sones' catheter. | Paracentesis. Judkins' catheter. | Paracentesis. Inventors' catheters for left/right coronary artery and venous bypass. |
| Without replacing of catheter, angiograph of right & left coronary artery and left ventricle | Separate catheter is necessary for left and right coronary artery and left ventricle, each. | Without replacing the catheter, left/right coronary arteries are enabled. Separate catheter is necessary for ventricle angiography. |
| Training needed for catheter operation. | Operation of catheter is relatively easy. | Operation of catheter is relatively easy. |
| Surgical techniques are needed. | Surgical techniques are unnecessary | Surgical techniques are unnecessary. |
| Insertion opening for catheter is closed by sutration, and repeated insertion through the same region is impossible. | Debleeding by pressurizing. | Debleeding by pressurizing. No incision allows repeated insertion of catheter through the same region. |
| Almost no hematoma or bleeding, but may cause arterial obliteration due to thrombus. | Possibility of hematoma or after-bleeding. | Minimized possibility of hematoma or after-bleeding. |
| After operation, requiring extension of bracium, and brachial relaxation for about an hour. | Needed rest quiet in bed is 12 to 24 hours after operation. | Needed rest quiet is only an hour in bed and 3 hours for brachial relaxation. |
| Principally, 8 Fr catheter is used. | Principally, 6 Fr catheter is used. | Principally, 5 Fr and 5.2 Fr catheter are used. |

By only puncturing a paracentetic tube into the brachial artery, a minor wound is formed on the artery. Further, use of a thin catheter leaves only a minor wound compared with the Sones method which requires incision of the skin to expose the artery.

Since it is a brachial artery which is punctured by the paracentetic tube, patient movement after removal of the tube does not often result in bleeding caused by pressurization. Quiet rest is required only one hour or so after the procedure.

For the reason that the distance from the brachium to the heart is greater than that between the femoral region and the heart, a short catheter can be used, providing preferred operability and requiring largely shortened time for angiographic inspection. In practice, only one-half of the time is needed compared with that needed in insertion through the femoral region.

For reasons mentioned above, the present invention is suitable for the cases which require repeated angiographic operations.

EXAMPLES OF CASES

EXAMPLE 1

A patient Y.K., 70 years old. In 1966, the patient was hospitalized owing to crisis of myocardial infarction. Since 1987, an intermittent claudication as an arterial obliteration occurred.

In December 1987, angiography performed for the first time and hospitalized for 10 days. As a result, stenoisis was found in the coronary artery, and the abdominal aorta was completely obliterated in its lower region. The time needed for inspection was 65 minutes, that for X-ray examination was 20.4 minutes, and the rest quiet time after operation was one hour.

In November 1991, the coronary arterial angiography of the second time was performed for review of the proceeding and paracentesis, and the patient was hospitalized for three days. The inspection having the same contents as those in the first inspection was performed as follows: pressing the right brachium, inserting a paracentetic tube, using a catheter of the inventors' type prepared in use for right and left coronary arteries and a conventional 5-inch pigtail catheter. The time required for examination was 45 minutes, which was remarkable compared with the first operation. Together with one hour for rest, the burden borne by the patient was clearly reduced. The case could not be made from the femoral artery by Judkins' method because of the obliterated abdominal aorta.

EXAMPLE 2

A patient T.F., 62 years old. Since 1985, the patient had a crisis of stenocardia. In both January 1985 and January 1988, respectively, coronary angiography was performed by Sones method through incision of the right brachium to the artery.

In March 1993, a third coronary angiography was performed through incision of the right brachium and using the inventors' catheters for use in right and left coronary arteries, where the necessary time for examination was 42 minutes and roentgenoscopy was 7.2 minutes. Thus, each time was remarkably reduced compared with that of the first and second operations.

Thereafter, the lesion worsened, and operations of the coronary arterial bypass surgery were performed on three regions, including those on the venous bypass, the left internal thoracic arterial bypass, and the gastroepiploic artery.

In June 1993, another coronary angiography was performed for confirming the existence of the openness of the bypass after the previous operation, with the patient being hospitalized after operation. The angiography was performed: (a) in the left and right coronary arteries and vein bypass, using the inventors' type catheter of left and right coronary arterial use; (b) in the internal thoracic artery and venous bypass, using a catheter of internal thoracic arterial use; and (c) in the gastroepiploic arterial bypass, using a catheter of gastroepiploic arterial use. Although the number of catheters for performing angiography was increased, the time required was reduced to 55 minutes for the operation, 14.4 minutes for roentgenoscopy, plus one hour for the patient to take rest after the operation.

Paracentesis, the technique which has been already established, is not as difficult as the incision catheter is also easily acquired even by a beginner in a relatively short time since it is formed in a shape easily inserted into any artery. Further, the patient would not feel ashamed using a brachial region.

Angiography of right and left coronary artery and vein bypass is performed using only one catheter. Also, angiography of the internal thoracic artery as well as that of the gastroepiploic artery, which were in the past normally performed only through the femoral region, are all performed through the brachial region by changing the catheter. In these cases, a catheter, suitable for the respective artery, may be selected from the above-mentioned catheters "a", "b", and "c"

For reasons mentioned above, artery angiography in outpatient sites or in mobile angiography using automobiles may also be performed.

Only a small number of catheters may be used to enable angiography to be performed at the outpatient sites, thereby saving the costs of medical expenses.

Any case of arterial obliteration, such as a clogged abdominal artery or femoral artery, may be also examined.

In summary, the present invention reduces the burden on the patient who is subject to the surgery and, may be used for cases requiring repeated process of angiography. The techniques necessary for including catheters are acquired in a comparatively short period of time.

Angiography is performed with only one catheter for the right coronary artery as well as venous bypass; and, by replacement of catheters, for the internal thoracic and gastroepioploic arteries, and all of the above can be performed through the brachial approach, and also performed in outpatient sites as well as mobile surgery using automobiles. Also, all the treatments above are cheaper to perform.

What is claimed is:

1. A method of angiography of a coronary artery, a venous bypass, a gastroepiploic artery or an internal thoracic artery by means of brachial paracentesis, comprising the steps of:

puncturing a paracentetic tube into the brachial artery; and inserting through said paracentetic tube an improved thin catheter selected from the group consisting of:

(a) a catheter of the type in use for the left and right coronary artery and venous bypass;

(b) a catheter of the type in use for the internal thoracic artery; and (c) a catheter of the type in use for the gastroepiploic artery.

2. A method of angiography of a coronary artery, a venous bypass, a gastroepiploic artery or an internal thoracic artery by means of brachial paracentesis, comprising the steps of:

puncturing a paracentetic tube into the brachial artery; and inserting through said paracentetic tube an improved thin catheter selected from the group consisting of:

(a) a catheter of the type in use for the left and right coronary artery and venous bypass having an elongated tubing and a tip end substantially perpendicularly extending from one end of said tubing;

(b) a catheter of the type in use for the internal thoracic artery having an elongated tubing and a tip end arcuately extending from one end of said tubing; and (c) a catheter of the type in use for the gastroepiploic artery having an elongated tubing and a tip end extending and slightly curved from one end of said tubing.

* * * * *

UNITED STATES PATENT AND TRADEMARK OFFICE
CERTIFICATE OF CORRECTION

PATENT NO. : 5,471,986
DATED : December 5, 1995
INVENTOR(S) : Takao Ishimura et al It is certified that error appears in the above-indentified patent and that said Letters Patent is hereby corrected as shown below:

Column 4, line 59; after "incision", insert --technique in Sones method, and operation of the--.

Column 5, line 5, after "c", insert --.--.

Signed and Sealed this

Second Day of April, 1996

Attest:

BRUCE LEHMAN

*Attesting Officer*     *Commissioner of Patents and Trademarks*